(12) United States Patent
DiGiore et al.

(10) Patent No.: US 8,428,746 B2
(45) Date of Patent: Apr. 23, 2013

(54) MOLDABLE CHARGER WITH SHAPE-SENSING MEANS FOR AN IMPLANTABLE PULSE GENERATOR

(75) Inventors: Andrew DiGiore, Santa Monica, CA (US); Brett Schleicher, Valencia, CA (US); Greg Baldwin, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/569,027

(22) Filed: Aug. 7, 2012

(65) Prior Publication Data

US 2013/0046361 A1   Feb. 21, 2013

Related U.S. Application Data

(63) Continuation of application No. 12/495,645, filed on Jun. 30, 2009, now Pat. No. 8,260,432.

(51) Int. Cl.
*A61N 1/00* (2006.01)
(52) U.S. Cl.
USPC .......................................................... 607/61
(58) Field of Classification Search .................... 607/60, 607/61
See application file for complete search history.

(56) References Cited

U.S. PATENT DOCUMENTS

| | | |
|---|---|---|
| 4,082,097 A | 4/1978 | Mann et al. |
| 4,981,141 A | 1/1991 | Segalowitz |
| 5,168,814 A | 12/1992 | Kuzuya et al. |
| 5,307,818 A | 5/1994 | Segalowitz |
| 5,483,967 A | 1/1996 | Ohtake |
| 5,545,191 A | 8/1996 | Mann et al. |
| 5,674,249 A | 10/1997 | de Coriolis et al. |
| 5,690,693 A | 11/1997 | Wang et al. |
| 5,702,431 A | 12/1997 | Wang et al. |
| 5,759,199 A | 6/1998 | Snell et al. |
| 5,862,803 A | 1/1999 | Besson et al. |
| 5,933,002 A | 8/1999 | Jacobsen et al. |
| 5,948,006 A | 9/1999 | Mann |

(Continued)

FOREIGN PATENT DOCUMENTS

| | | |
|---|---|---|
| EP | 1303332 A1 | 12/2004 |
| EP | 2046446 A1 | 1/2008 |

(Continued)

OTHER PUBLICATIONS

File History of U.S. Appl. No. 12/495,605, filed Jun. 30, 2009, Applicant: Andrew DiGiore.

(Continued)

*Primary Examiner* — George Manuel
*Assistant Examiner* — Robert N Wieland
(74) *Attorney, Agent, or Firm* — Vista IP Law Group LLP

(57) ABSTRACT

Electrical energy is transcutaneously transmitted from an external charger to an implanted medical device. The external charger includes a charging head that is selectively shapeable to conform to the surface of a patient to enhance charge efficiency and patient comfort. An alternating current charging coil is housed in the charging head and configured for transcutaneously transmitting electrical energy to the implanted medical device. The shape of the coil is changeable as the charging head is shaped, and at least one sensor determines changes in the shape of the charging coil and causes the charge of the coil to be adjusted based on the coil shape.

7 Claims, 9 Drawing Sheets

U.S. PATENT DOCUMENTS

| | | |
|---|---|---|
| 5,959,529 A | 9/1999 | Kail, IV |
| 6,076,016 A | 6/2000 | Feierbach |
| 6,181,965 B1 | 1/2001 | Loeb et al. |
| 6,225,901 B1 | 5/2001 | Kail, IV |
| 6,263,245 B1 | 7/2001 | Snell |
| 6,275,736 B1 | 8/2001 | Kuzma et al. |
| 6,315,719 B1 | 11/2001 | Rode et al. |
| 6,516,227 B1 | 2/2003 | Meadows et al. |
| 6,553,263 B1 | 4/2003 | Meadows et al. |
| 6,561,975 B1 | 5/2003 | Pool et al. |
| 6,571,128 B2 | 5/2003 | Lebel et al. |
| 6,574,511 B2 | 6/2003 | Lee |
| 6,577,899 B2 | 6/2003 | Lebel et al. |
| 6,577,901 B2 | 6/2003 | Thompson |
| 6,589,244 B1 | 7/2003 | Sevrain et al. |
| 6,628,989 B1 | 9/2003 | Penner et al. |
| 6,636,769 B2 | 10/2003 | Govari et al. |
| 6,647,298 B2 | 11/2003 | Abrahamson et al. |
| 6,704,602 B2 | 3/2004 | Berg et al. |
| 6,723,045 B2 | 4/2004 | Cosentino et al. |
| 6,738,671 B2 | 5/2004 | Christophersom et al. |
| 6,804,554 B2 | 10/2004 | Ujhelyi et al. |
| 6,804,558 B2 | 10/2004 | Haller et al. |
| 6,895,281 B1 | 5/2005 | Amundson et al. |
| 6,897,788 B2 | 5/2005 | Khair et al. |
| 6,940,403 B2 | 9/2005 | Kail, IV |
| 7,003,353 B1 | 2/2006 | Parkhouse |
| 7,024,248 B2 | 4/2006 | Penner et al. |
| 7,054,691 B1 | 5/2006 | Kuzma et al. |
| 7,107,103 B2 | 9/2006 | Schulman et al. |
| 7,177,690 B2 | 2/2007 | Woods et al. |
| 7,184,836 B1 | 2/2007 | Meadows et al. |
| 7,191,013 B1 | 3/2007 | Miranda et al. |
| 7,225,032 B2 | 5/2007 | Schmeling et al. |
| 7,286,880 B2 | 10/2007 | Olson et al. |
| 7,286,881 B2 | 10/2007 | Schommer et al. |
| 7,289,855 B2 | 10/2007 | Nghiem et al. |
| 7,308,316 B2 | 12/2007 | Schommer |
| 7,338,434 B1 | 3/2008 | Haarstad et al. |
| 7,392,091 B2 | 6/2008 | Bruinsma |
| 7,392,092 B2 | 6/2008 | Li et al. |
| 7,409,245 B1 | 8/2008 | Larson et al. |
| 2002/0087204 A1* | 7/2002 | Kung et al. ............ 607/61 |
| 2003/0120323 A1 | 6/2003 | Meadows et al. |
| 2004/0147972 A1 | 7/2004 | Greatbatch et al. |
| 2005/0075693 A1 | 4/2005 | Toy et al. |
| 2005/0075694 A1 | 4/2005 | Schmeling et al. |
| 2005/0075695 A1 | 4/2005 | Schommer |
| 2005/0075696 A1 | 4/2005 | Forsberg et al. |
| 2005/0075697 A1 | 4/2005 | Olson et al. |
| 2005/0075699 A1 | 4/2005 | Olson et al. |
| 2005/0075700 A1 | 4/2005 | Schommer et al. |
| 2005/0113889 A1 | 5/2005 | Jimenez et al. |
| 2006/0008967 A1 | 1/2006 | Polk, Jr. et al. |
| 2006/0020306 A1 | 1/2006 | Davis et al. |
| 2006/0093894 A1 | 5/2006 | Scott et al. |
| 2007/0032839 A1 | 2/2007 | Parramon et al. |
| 2007/0096686 A1 | 5/2007 | Jimenez et al. |
| 2007/0167997 A1 | 7/2007 | Forsberg et al. |
| 2007/0255223 A1 | 11/2007 | Phillips et al. |
| 2007/0276450 A1 | 11/2007 | Meadows et al. |
| 2007/0293914 A1 | 12/2007 | Woods et al. |
| 2008/0014022 A1 | 1/2008 | Wroblewski et al. |
| 2008/0027500 A1 | 1/2008 | Chen |
| 2008/0051855 A1 | 2/2008 | Schommer |
| 2008/0097554 A1 | 4/2008 | Payne et al. |
| 2008/0103543 A1 | 5/2008 | Li et al. |
| 2008/0103557 A1 | 5/2008 | Davis et al. |
| 2008/0172109 A1 | 7/2008 | Rahman et al. |
| 2008/0276684 A1 | 11/2008 | Goldbach |
| 2008/0281379 A1 | 11/2008 | Wesselink |
| 2008/0288025 A1 | 11/2008 | Peterson |
| 2008/0306569 A1 | 12/2008 | Tobacman |
| 2009/0082835 A1 | 3/2009 | Jaax et al. |
| 2009/0088812 A1 | 4/2009 | Wulfman |
| 2009/0118796 A1 | 5/2009 | Chen et al. |
| 2009/0174206 A1 | 7/2009 | Vander Sluis et al. |
| 2010/0106223 A1 | 4/2010 | Grevious et al. |
| 2010/0119416 A1 | 5/2010 | Tajima |
| 2010/0331917 A1 | 12/2010 | DiGiore |
| 2010/0331918 A1 | 12/2010 | DiGiore |
| 2010/0331919 A1 | 12/2010 | DiGiore |
| 2011/0205083 A1 | 8/2011 | Janna et al. |

FOREIGN PATENT DOCUMENTS

| | | |
|---|---|---|
| EP | 2077898 A1 | 4/2008 |
| WO | WO 96/40367 A1 | 12/1996 |
| WO | WO 98/11942 A1 | 3/1998 |
| WO | WO 00/69012 A1 | 11/2000 |
| WO | WO 2004/068615 A2 | 8/2004 |
| WO | WO 2005/039697 A1 | 5/2005 |
| WO | WO 2006/012371 A1 | 2/2006 |
| WO | WO 2006/014971 A2 | 2/2006 |
| WO | WO 2006/022645 A1 | 3/2006 |
| WO | WO 2006/050117 A2 | 5/2006 |
| WO | WO 2008/014022 A1 | 1/2008 |
| WO | WO 2008/048724 A1 | 4/2008 |
| WO | WO 2008/054437 A1 | 5/2008 |
| WO | WO 2008/054447 A1 | 5/2008 |
| WO | WO 2008/143857 A1 | 11/2008 |
| WO | WO 2009/042063 A1 | 4/2009 |
| WO | WO 2009/055203 A1 | 4/2009 |
| WO | WO 2009/061537 A1 | 5/2009 |

OTHER PUBLICATIONS

Non-Final Office Action dated Jun. 20, 2011 in U.S. Appl. No. 12/495,605, filed Jun. 30, 2009, Applicant: Andrew DiGiore, (24 pages).

File History of U.S. Appl. No. 12/495,575, filed Jun. 30, 2009, Applicant: Andrew DiGiore.

Non-Final Office Action dated Jun. 21, 2011 in U.S. Appl. No. 12/495,575, filed Jun. 30, 2009, Applicant: Andrew DiGiore, (24 pages).

File History of U.S. Appl. No. 12/495,523, filed Jun. 30, 2009, Applicant: Andrew DiGiore.

Non-Final Office Action dated Jun. 20, 2011 in U.S. Appl. No. 12/495,523, filed Jun. 30, 2009, Applicant: Andrew DiGiore, (25 pages).

Non-Final Office Action dated Jan. 12, 2012 in U.S. Appl. No. 12/495,523, filed Jun. 30, 2009, inventor: Andrew DiGiore, (28pages).

Non-Final Office Action dated Jan. 4, 2012 in U.S. Appl. No. 12/495,575, filed Jun. 30, 2009, inventor: Andrew DiGiore, (27pages).

Non-Final Office Action dated Dec. 9, 2011 in U.S. Appl. No. 12/495,605, filed Jun. 30, 2009, inventor: Andrew DiGiore, (24pages).

* cited by examiner

MOLDABLE CHARGER WITH SHAPE-SENSING MEANS FOR AN IMPLANTABLE PULSE GENERATOR

RELATED APPLICATION DATA

This application is a continuation of U.S. patent application Ser. No. 12/495,645, filed Jun. 30, 2009, now U.S. Pat. No. 8,260,432 which application is expressly incorporated by reference herein.

FIELD OF THE INVENTION

The present invention relates to external charging devices for implantable devices, and more particularly, to devices for transcutaneously recharging devices implanted within patients.

BACKGROUND OF THE INVENTION

Implantable stimulation devices are devices that generate and deliver electrical stimuli to body nerves and tissues for the therapy of various biological disorders, such as: pacemakers to treat cardiac arrhythmia; defibrillators to treat cardiac fibrillation; cochlear stimulators to treat deafness; retinal stimulators to treat blindness; muscle stimulators to produce coordinated limb movement; spinal cord stimulators to treat chronic pain; cortical and deep brain stimulators to treat motor and psychological disorders; and other neural stimulators to treat urinary incontinence, sleep apnea, shoulder sublaxation, etc. The present invention may find applicability in all such applications, although the description that follows will generally focus on the use of the invention within a spinal cord stimulation system, such as that disclosed in U.S. Pat. No. 6,516,227 ("the '227 patent"), issued Feb. 4, 2003 in the name of inventors Paul Meadows et al., which is incorporated herein by reference in its entirety.

As an alternative to having a lead or wire pass through the skin of the patient, power and/or data can be supplied to an implanted medical device via an RF or electromagnetic link that couples power from an external (non-implanted) coil to an internal (implanted) coil. So long as a suitable link, e.g., an inductive link, is established between these two coils, which means some sort of external power source must be carried by or worn by the patient, power and/or data can be continuously supplied to the implanted medical device from the worn or carried external device, thereby allowing the implanted medical device to perform its intended function.

It is also known to power an implanted medical device with a battery that is housed internal to the implanted device. However, any battery used for extended periods of time will eventually need to be either recharged or replaced. Replacing an internally implanted battery may subject the patient to further surgery and thus is not desirable, at least not on a frequent basis.

Rather than replace an implanted battery, the battery can be recharged by transcutaneously coupling power from an external source to an implanted receiver that is connected to the battery. Although power can be coupled from an external source at radio frequencies using matching antennas, it is generally more efficient to employ an external transmission coil and an internal receiving coil which are inductively (electromagnetically) coupled to each other to transfer power at lower frequencies. In this approach, the external transmission coil is energized with alternating current (AC), producing a varying magnetic flux that passes through the patient's skin and induces a corresponding AC voltage in the internal receiving coil. The voltage induced in the receiving coil may then be rectified and used to power the implanted device and/or to charge a battery or other charge storage device (e.g., an ultracapacitor), which in turn powers the implanted device. For example, U.S. Pat. No. 4,082,097 discloses a system for charging a rechargeable battery in an implanted human tissue stimulator by means on an external power source.

To allow for flexibility of use and increased comfort to a patient as the implanted battery is charged, the patient would benefit from a convenient unobtrusive external charging device that transmits power transcutaneously to an implanted device, wherein such external charging device is not only small and lightweight, but is also readily conformable to the patient in close proximity to the implanted device. For example, the device could be constructed such that it could be formed to any shape when needed, or the device could be constructed to be shaped in one particular form and then remain in that form for frequent use on the same area of the patient.

In shaping such an external charging device to fit the patient, it is also important to consider the shape of the charging coil in the external charging device. In particular, if the shape of the charging coil in the external charging device changes as the external charging device is shaped to conform to the patient, the characteristics of the charge from the charging coil may change, possibly negatively impacting the coupling factor of the external charging device and the IPG and thus the efficiency of the charging action. Not only does good coupling increase the power transferred from the external charger to the implantable pulse generator, it also minimizes heating in the implantable pulse generator. This in turn reduces the power requirements of the external charger, which reduces heating of the external charger and minimizes the smaller form factor of the external charger. As such, maintaining good coupling may be achieved by monitoring any change in the shape of the coil and subsequently adjusting power requirements of the external charger.

Thus, there remains a need for improved devices and methods for shapeable devices that conform to a surface of the patient while also ensuring that changes in the shape of the charging coil do not negatively impact the charging action of the implanted device.

SUMMARY OF THE INVENTION

In accordance with the present invention, an external charger for an implantable medical device is provided. The external charger comprises a charging head that is selectively shapeable to conform to a surface of a patient. The external charger also comprises an alternating current (AC) charging coil housed in the body and configured for transcutaneously transmitting electrical energy to the implanted medical device, wherein the shape of the coil is changeable as the body is shaped. The external charger further comprises at least one sensor, such as a strain gauge, for determining the shape of the coil. In one embodiment, the external charger further comprises a processor configured to adjust the charge of the coil in response to receiving signals from the sensor(s) regarding changes in the shape of the coil.

In another embodiment, a method of charging an implantable medical device with the external charger is provided, comprising placing the external charger on a surface of a patient in the general vicinity of the implantable device and transcutaneously transmitting energy from the coil to the implantable medical device. Additionally, the external charger is shaped to conform to the surface of the patient and adhered to the patient.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

At the outset, it is noted that the present invention may be used with an implantable pulse generator (IPG) or similar implanted electrical stimulator, which may be used as a component of numerous different types of stimulation systems. The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical and deep brain stimulator, peripheral nerve stimulator, or in any other neural stimulator configured to treat urinary incontinence, sleep apnea, shoulder sublaxation, etc.

Figure 1:
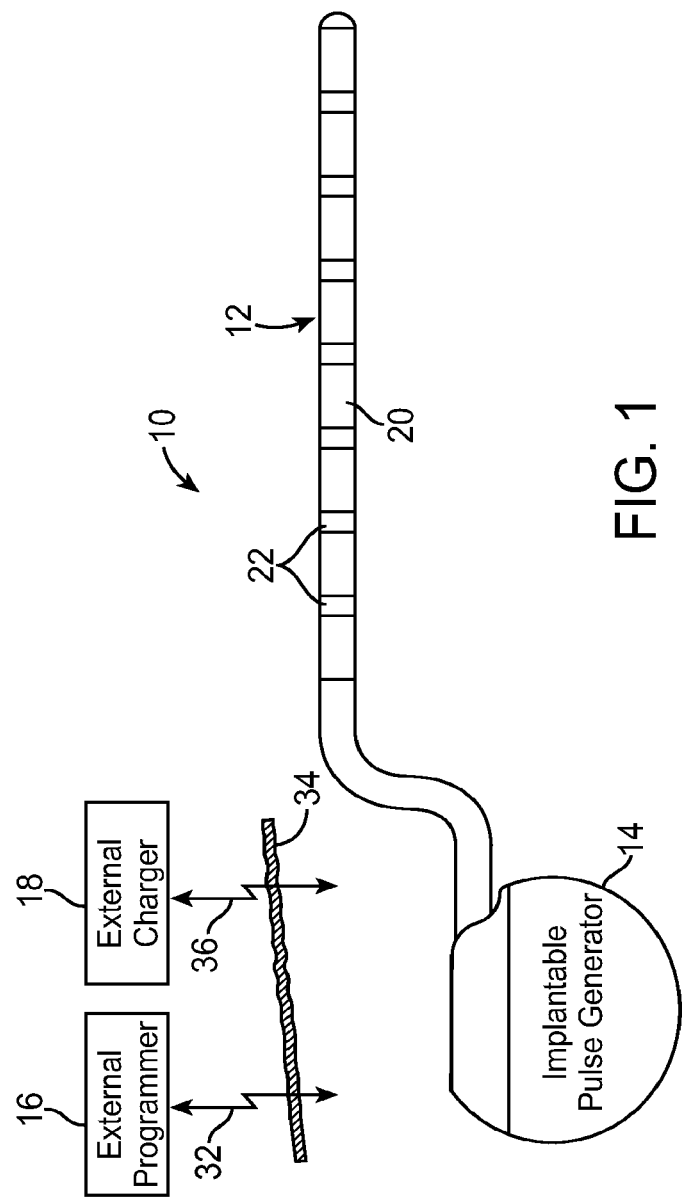
FIG. 1 is plan view of one embodiment of a spinal cord stimulation (SCS) system arranged in accordance with the present inventions.

Turning first to FIG. 1, an exemplary SCS system 10 generally comprises an implantable neurostimulation lead 12, an implantable pulse generator (IPG) 14, an external (non-implanted) programmer 16, and an external (non-implanted) charger 18. In the illustrated embodiment, the lead 12 is a percutaneous lead and, to that end, includes a plurality of in-line electrodes 20 carried on a flexible body 22. The IPG 14 is electrically coupled to the lead 12 in order to direct electrical stimulation energy to each of the electrodes 20.

The IPG 14 includes an outer case formed from an electrically conductive, biocompatible material, such as titanium. The case forms a hermetically sealed compartment wherein the electronic and other components are protected from the body tissue and fluids. While a portion of the electronic components of the IPG 14 will be described in further detail below, additional details of the IPG 14, including the battery, antenna coil, and telemetry and charging circuitry, are disclosed in U.S. Pat. No. 6,516,227, which is expressly incorporated herein by reference.

Figure 2:
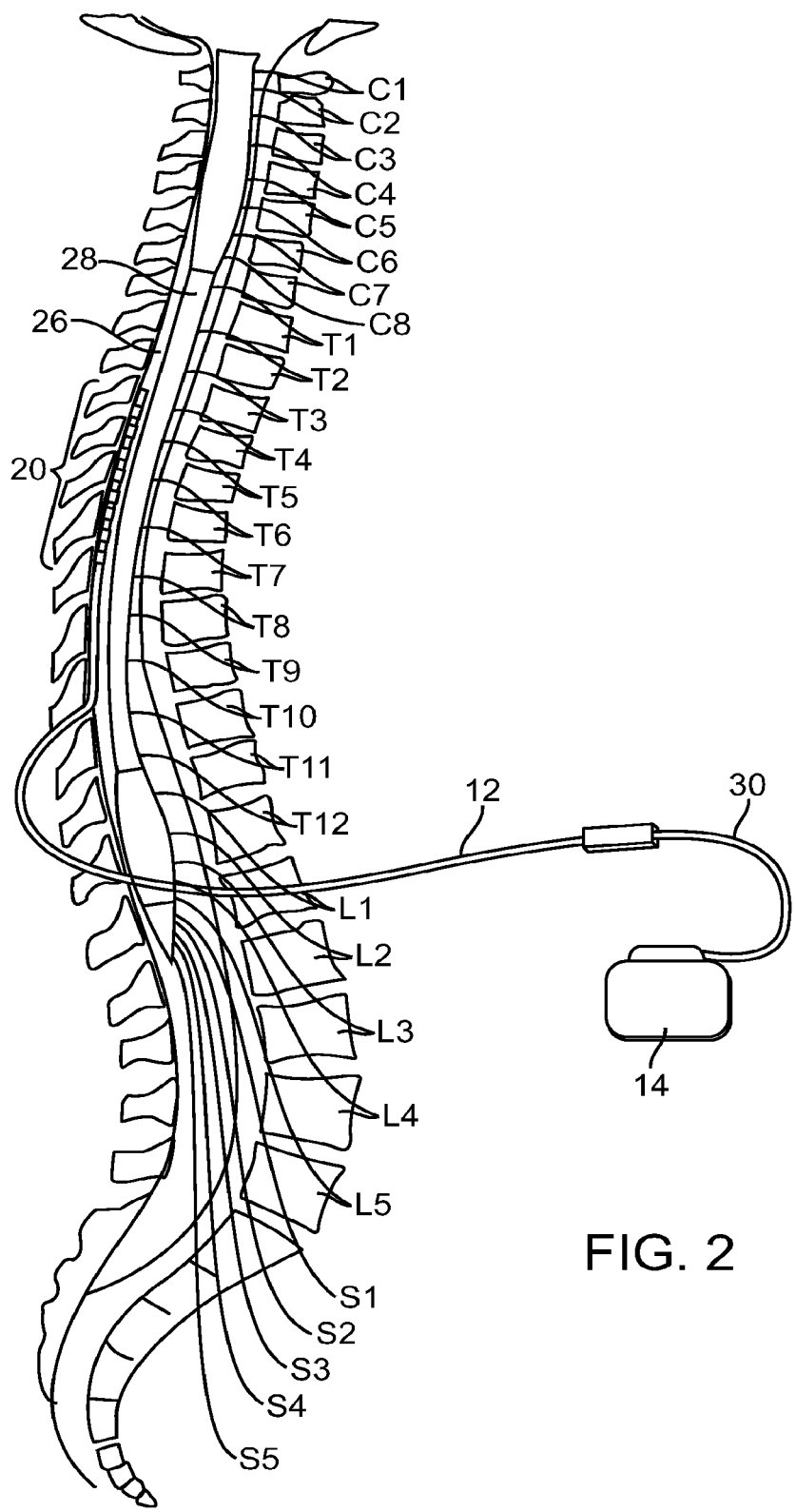
FIG. 2 is a plan view of the SCS system of FIG. 1 in use with a patient.

As shown in FIG. 2, the neurostimulation lead 12 is implanted within the epidural space 26 of a patient through the use of a percutaneous needle or other convention technique, so as to be in close proximity to the spinal cord 28. Once in place, the electrodes 20 may be used to supply stimulation energy to the spinal cord 28 or nerve roots. The preferred placement of the lead 12 is such that the electrodes 20 are adjacent, i.e., resting upon, the nerve area to be stimulated. The IPG 14 may be implanted in various suitable locations of the patient's body, such as in a surgically-made pocket either in the abdomen or above the buttocks. A lead extension 30 may facilitate locating the IPG 14 away from the exit point of the lead 12.

Referring back to FIG. 1, the IPG 14 is programmed, or controlled, through the use of the external programmer 16. The external programmer 16 is transcutaneously coupled to the IPG 14 through a suitable communications link (represented by the arrow 32) that passes through the patient's skin 34. Suitable links include, but are not limited to radio frequency (RF) links, inductive links, optical links, and magnetic links. For purposes of brevity, the electronic components of the external programmer 16 will not be described herein. Details of the external programmer, including the control circuitry, processing circuitry, and telemetry circuitry, are disclosed in U.S. Pat. No. 6,516,227, which has been previously incorporated herein by reference.

The external charger 18 is transcutaneously coupled to the IPG 14 through a suitable link (represented by the arrow 36) that passes through the patient's skin 34, thereby coupling power to the IPG 14 for the purpose of operating the IPG 14 or replenishing a power source, such as a rechargeable battery (e.g., a Lithium Ion battery), within the IPG 14. In the illustrated embodiment, the link 36 is an inductive link; that is, energy from the external charger 18 is coupled to the battery within the IPG 14 via electromagnetic coupling. Once power is induced in the charging coil in the IPG 14, charge control circuitry within the IPG 14 provides the power charging protocol to charge the battery.

Once the IPG 14 has been programmed, and its power source has been charged or otherwise replenished, the IPG 14 may function as programmed without the external programmer 16 or the external charger 18 being present. While the external programmer 16 and external charger 18 are described herein as two separate and distinct units, it should be appreciated that the functionality of the external programmer 16 and external charger 18 can be combined into a single unit. It should be noted that rather than an IPG, the system 10 may alternatively utilize an implantable receiver-stimulator (not shown) connected to lead 12. In this case, the power source, e.g., a battery, for powering the implanted receiver, as well as control circuitry to command the receiver-stimulator, will be contained in an external controller/charger inductively coupled to the receiver-stimulator via an electromagnetic link.

Figure 3:
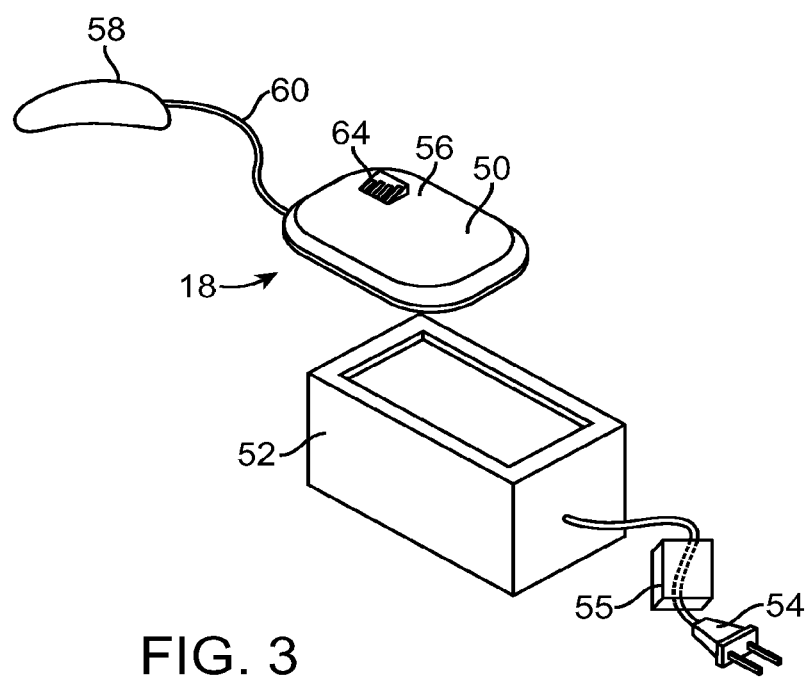
FIG. 3 is a perspective view of an external charger used in the SCS system.

Referring now to FIG. 3, the external components of the external charger 18 will now be described. In this embodiment, the external charger 18 takes the form of a two-part system comprising a portable charger 50 and a charging base station 52. The charging base station 52 includes an AC plug 54, so that it can be easily plugged into any standard 110 volt alternating current (VAC) or 200 VAC outlet. The charging base station 52 further includes an AC/DC transformer 55, which provides a suitable DC voltage (e.g., 5 VDC) to the circuitry within the charging base station 52.

The portable charger 50 includes a housing 56 for containing circuitry, and in particular, the recharging circuitry and battery (not shown in FIG. 3), which will be discussed in further detail below. The housing 56 is shaped and designed in a manner that allows the portable charger 50 to be detachably inserted into the charging base station 52 and returned to the charging base station 52 between uses, thereby allowing the portable charger 50, itself, to be recharged. Thus, both the IPG 14 and the portable charger 50 are rechargeable. The portable charger 50 may be returned to the charging base station 52 between uses. Also, the portable charger 50 may be carried on the patient, e.g., in a pouch strapped to the patient, or placed near the patient.

In the illustrated embodiment, the portable charger 50 includes a charging head 58 connected to the housing 56 by way of a suitable flexible cable 60. For purposes of illustration, the charging head 58 is shown in this embodiment as having a curvaceous shape and is also flexible, more details of which will be provided below. The charging head 58 houses an antenna 82, and in particular an AC coil 82 (see FIGS. 5A and 5B), which will also be described in more detail below. The coil 82 transmits the charging energy to the IPG 14. In an alternative embodiment, the portable charger 50 does not include a separate charging head, but instead includes a single housing that contains the recharging circuitry, battery, and AC coil.

Figure 4:
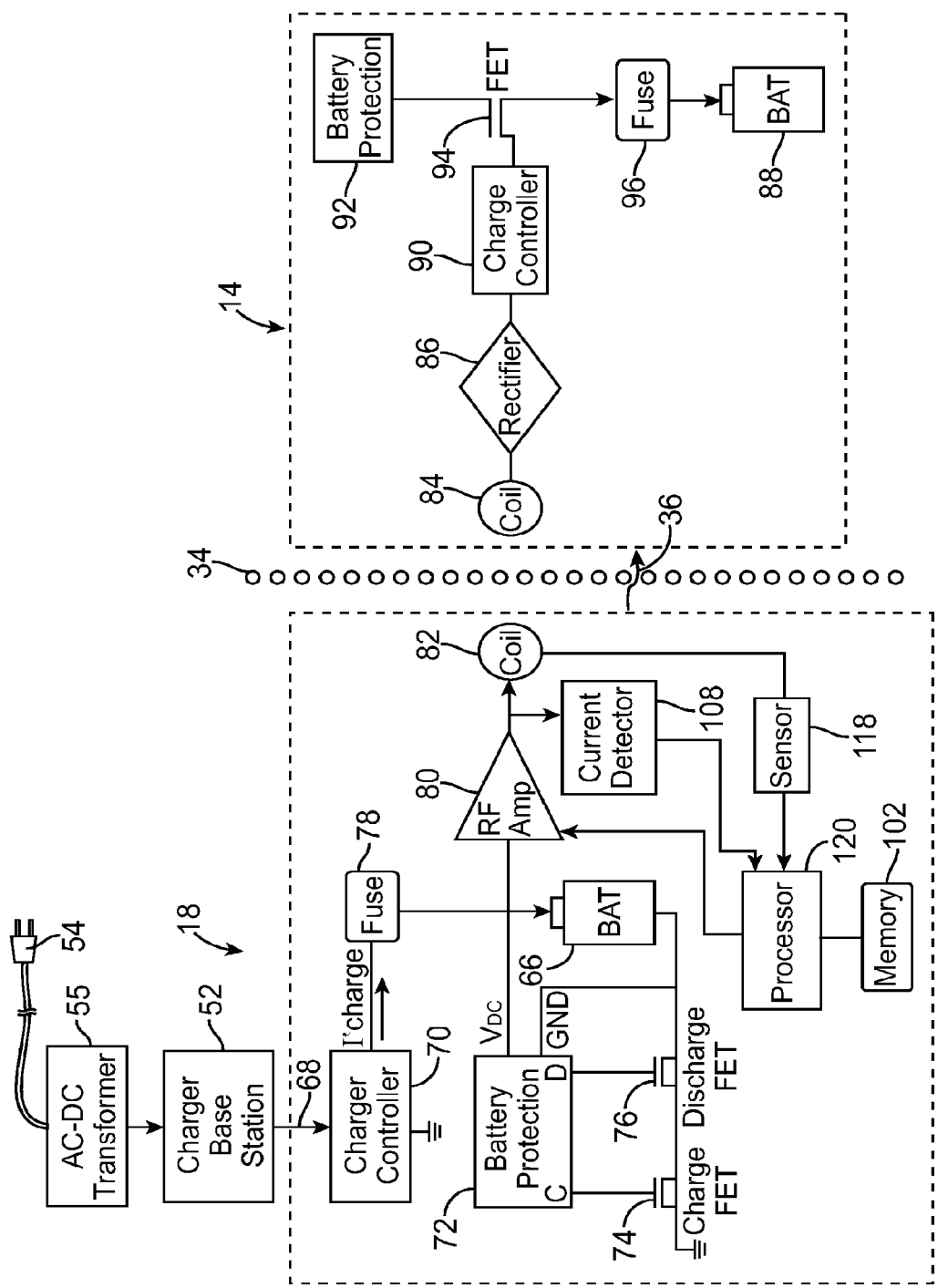
FIG. 4 is a block diagram of the internal components of one embodiment of an external charger and implantable pulse generator used in the SCS system of FIG. 1.

Referring to FIG. 4, the recharging elements of the IPG 14 and external charger 18 will now be described. It should be noted that the diagram of FIG. 4 is functional only, and is not intended to be limiting. Those of skill in the art, given the descriptions presented herein, should be able to readily fashion numerous types of recharging circuits, or equivalent circuits, that carry out the functions indicated and described.

As previously discussed above, the external charger 18 and IPG 14 are inductively coupled together through the patient's skin 34 (shown by dotted line) via the inductive link 36 (shown by wavy arrow). The portable charger 50 includes a battery 66, which in the illustrated embodiment is a rechargeable battery, such as a Lithium Ion battery. When a recharge is needed, energy (shown by arrow 68) is coupled to the battery 66 via the charging base station 52 in a conventional manner. In the illustrated embodiment, the battery 66 is fully charged in approximately four hours. Once the battery 66 is fully charged, it has enough energy to fully recharge the battery of the IPG 14. If the portable charger 50 is not used and left on charger base station 52, the battery 66 will self-discharge at a rate of about 10% per month. Alternatively, the battery 66 may be a replaceable battery.

The portable charger 50 also includes: a charge controller 70, which serves to convert the DC power from an AC/DC transformer 55 to the proper charge current and voltage for the battery 66; a battery protection circuit 72, which monitors the voltage and current of the battery 66 to ensure safe operation via operation of FET switches 74, 76; a fuse 78 that disconnects the battery 66 in response to an excessive current condition that occurs over an extended period of time; a power amplifier 80, and in particular a radio frequency (RF) amplifier, for converting the DC power from the battery 66 to a large alternating current; and an electrical current detector 108 that measures the magnitude of the electrical current input from the power amplifier 80 into the coil 82, and continually outputs the measured magnitudes to a processor 120 as the frequency of the current is varied. Further details discussing this control and protection circuitry are described in U.S. Pat. No. 6,516,227, which has been previously incorporated herein by reference.

As will be described in further detail below, the charging head 58 is flexible so as to be selectively shaped to conform to a patient. To allow for such flexibility, the coil 82 may change shape as the charging head is shaped 58. However, a change in the shape of the coil may decrease the efficiency of energy transfer from the charging head 58 to the IPG 14. Thus, to monitor changes in the shape of the coil 82, the charging head 58 includes one or more sensors 118, e.g., one or more strain gauges, in communication with the coil 82. The sensors 118 may monitor the shape of the coil 82 on a continuous or intermittent basis, or on a discrete basis as selectively determined by manual operation (e.g., via a communication system used by medical personnel). The sensors 118 then communicate the shape of the coil 82 to the processor 120, or optionally a separate processor. The processor 120 then communicates directly or indirectly to the coil 82, e.g., through the amplifier 80 and/or a separate programmer, to raise or lower the frequency of the charge delivered from the coil 82 to the IPG 14 to maintain charge efficiency based on the changed shape of the coil 82.

For example, if the sensors 118 determine that the coil 82 is curved a certain amount as the charging head 58 is shaped, the sensors 118 communicate the change in the shape of the coil 82 to the processor 120. The processor 120 then adjusts the charging frequency of the coil 82 to a value corresponding to the changed shape of the coil 82. To this end, the processor 120 may include a memory component 102 (see FIG. 4) with a program that correlates the shape of the coil 82 with resistance in the coil 82 and then determines the needed adjustment in the charging frequency of the coil 82 to maintain an efficient charge rate of the IPG 14. Other features regarding the parts, circuitry, and operation of the sensors 118 and the processor 120 are known and understood in the art and thus, for purposes of brevity, are not included here.

To further ensure efficient transfer of energy to the IPG 14, the external charger 18 may include a bar charge indicator (not shown) located on the portable charger 50 or on the charging head 58, which provides a visual indication in the form of bars of the charging strength between the coil 82 and the IPG 14. The bar charge indicator may also signal to the user whether the coil 82 is properly aligned with the IPG 14. The external charger 18 may further include a misalignment indicator (not shown) located on the charging head 58 that provides an audible or tactile indication when the coil 82 is misaligned relative to the IPG 14. Alternatively, the misalignment indicator will generate an audible or tactile indication to indicate an alignment condition only when the charging head 58 is sufficiently aligned with the IPG 14. Once proper alignment with the IPG 14 has been achieved, as indicated by the bar charge indicator or misalignment indicator, the charging head 58 may be adhered to the patient's skin as described above. Details of the bar charge indicator and misalignment indicator are disclosed in U.S. patent application Ser. No. 11/748,436, which is expressly incorporated herein by reference.

Turning to the IPG, the IPG 14 includes an antenna 84, and in particular a coil, configured for receiving the alternating current from the external charger 18 via the inductive coupling. The coil 84 may be identical to, and preferably has the same resonant frequency as, the coil 82 of the external charger 18. The IPG 14 further comprises rectifier circuitry 86 for converting the alternating current back to DC power. The rectifier circuitry 86 may, e.g., take the form of a bridge rectifier circuit. The IPG 14 further includes a rechargeable battery 88, such as a Lithium Ion battery, which is charged by the DC power output by the rectifier circuitry 86. Typically, charging of the IPG 14 continues until the battery of the IPG 14 has been charged to at least 80% of capacity. In the illustrated embodiment, the battery 88 can be fully charged by the external charger 18 in under three hours (80% charge in two hours), at implant depths of up to 2.5 cm.

The IPG 14 also includes: a charge controller 90, which serves to convert the DC power from the rectifier circuitry 86 to the proper charge current and voltage for the battery 88; a battery protection circuit 92, which monitors the voltage and current of the battery 88 to ensure safe operation via operation of a FET switch 94; and a fuse 96 that disconnects the battery 88 in response to an excessive current condition that occurs over an extended period of time. Further details discussing this control and protection circuitry are described in U.S. Pat. No. 6,516,227, which has been previously incorporated herein by reference.

Figure 5A:
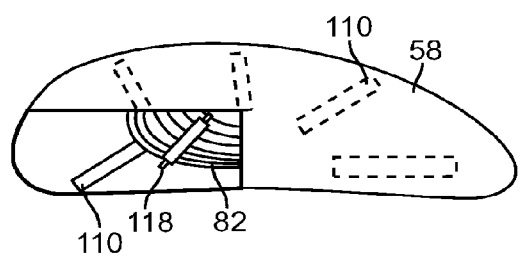
FIGS. 5A and 5B are perspective views with cut-outs of one embodiment of a charging head used in the SCS system of FIG. 1.
Figure 5B:
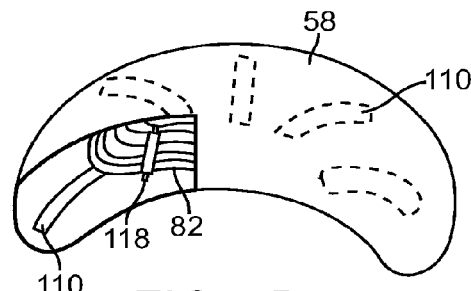

Referring now to FIGS. 5A and 5B, one embodiment of the charging head 58 will now be described. In this embodiment, the charging head 58 encases the coil 82 that is configured for transmitting the alternating current to the IPG 14 via inductive coupling. The coil 82 may comprise a 36 turn, single layer, 30 AWG copper air-core coil having a typical inductance of 45 $\mu$H and a DC resistance of about 1.15$\mu$. The coil 82 may be tuned for a resonance at 80 KHz with a parallel capacitor (not shown).

In the illustrated embodiment, the charging head 58 is formed from a flexible material that allows the charging head 58 to be selectively shaped as desired, e.g., by the user squeezing or bending the charging head 58 (see FIG. 5B). In this manner, the charging head 58 is shaped to conform to a bodily surface of the patient. The material forming the charging head 58 may, e.g., be composed of silicone, rubber, polyurethane, or a combination of these and/or similar materials.

The charging head 58 also includes a plurality of malleable support members 110 (some shown in phantom) that bend as the charging head 58 is shaped. Once the charging head 58 is shaped as desired, the support members 110 substantially maintain their bent form and thus help maintain the desired shape of the charging head 58, as shown in FIG. 5B. In other words, the support members 110 help to hold the charging head 58 in a fixed configuration until a physical force is applied to change the shape of the charging head 58.

Figure 6A:
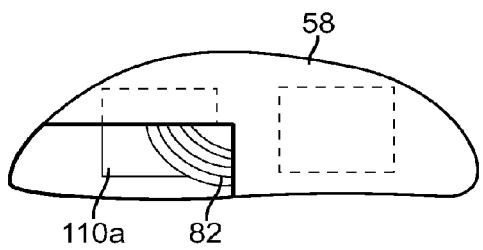
FIGS. 6A and 6B are perspective views with cut-outs of alternative embodiments of the charging head shown in FIGS. 5A and 5B.
Figure 6B:
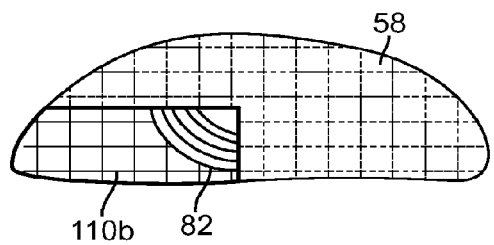

In the illustrated embodiment, the support members 110 form longitudinal ribs. In other embodiments, the support members 110 may form plates 110a (see FIG. 6A) or a mesh 110b (see FIG. 6B). The support members 110 may extend through the length of the charging head 58 or only a portion of the charging head 58. Also, the support members 110 may be formed of aluminum, plastic, or other suitable materials that do not impede the charging function of the external charger 18 while helping to support and maintain the shape of the charging head 58.

Figure 7A:
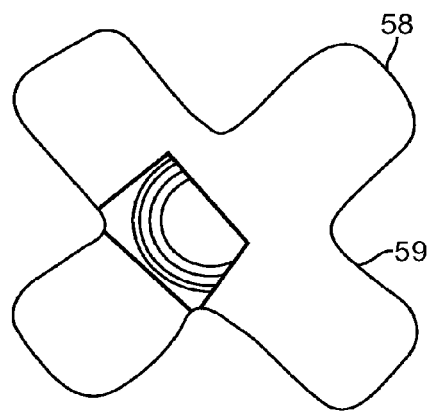
FIGS. 7A and 7B are perspective views of another alternative embodiment of the charging head shown in FIGS. 5A and 5B.
Figure 7B:
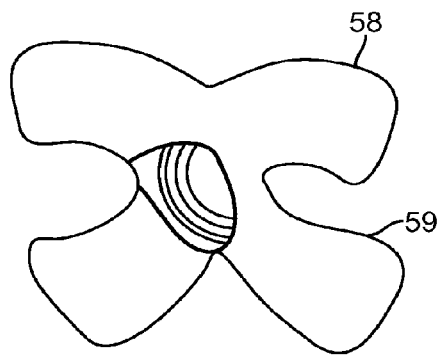

The charging head 58 may also have other structures, other than the elliptical structure shown in FIGS. 5A and 5B, which allow the charging head 58 to be bent into other shapes. For example, FIG. 7A illustrates an embodiment in which the charging head 58 has legs 59 in an X-shaped configuration, wherein the legs 59 can be bent toward each other, as shown in FIG. 7B. This embodiment may be particularly useful for encircling a patient's limb.

Because the charging head 58 can substantially conform to a surface of the patient, the efficiency with which the coil 82 charges the IPG 14 may be increased, as any gaps between the charger 18 and the patient's skin are minimized or eliminated. At the same time, the patient's comfort is enhanced, because the charging head 58 is shaped to suit the patient. However, as the charging head 58 is shaped, the shape of the coil 82 may change, which in turn may affect the charging efficiency of the coil 82.

To address such changes in charging efficiency, the charging head 58 includes the sensors 118, described above in reference to FIG. 4, to monitor changes in the shape of the coil 82. The sensors 118 may be placed over the coil 82 on one or both sides of the coil 82, and may also be affixed to the coil 82 with a suitable connector or adhesive. While the sensors 118 are illustrated on the embodiment of the charger head 58 shown in FIGS. 5A and 5B, the sensors 118 may also be used on the other embodiments described herein.

Figure 8A:
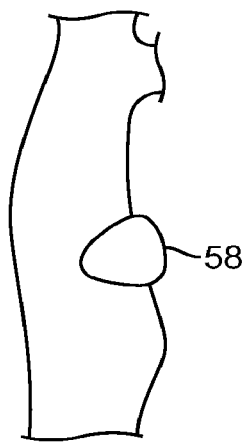
FIGS. 8A and 8B are perspective views of another alternative embodiment of a charging head, featuring a curable material, used in the SCS system of FIG. 1.
Figure 8B:
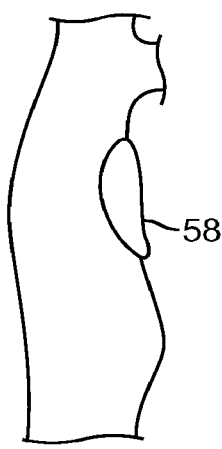

Referring to FIGS. 8A and 8B, another embodiment of the charging head 58 is initially formed from a flexible material that allows the charging head 58 to be selectively shaped as desired, as described above. In this case, however, the flexible material can be cured afterward, by heat-setting or other processes known in the art, such that the charging head 58 remains set in the selected shape. This embodiment may be particularly useful when a sturdier, less flexible, i.e., more permanent, form of the charging head 58 is desired. In one embodiment, the material forming the charging head 58 is substantially composed of a thermoset plastic.

Once the charging head 58 is shaped as desired, the thermoset plastic is cured using a suitable process known in the art, such as heat-setting or exposure to ultraviolet light, wherein the thermoset plastic maintains a fixed shape, as shown in FIG. 8A. In this embodiment, the thermoplastic cannot be re-cured and re-shaped and thus remains in the fixed shape. In another embodiment, the material forming the charging head 58 is substantially composed of a thermoplastic. In this embodiment, once the charging head 58 is shaped as desired, the thermoplastic is cured using a suitable process known in the art, such as by cooling or a catalyst chemical reaction. The thermoplastic maintains a fixed shape without any additional treatment but can later be heated, or other suitable processes can be used, to return the thermoplastic to a flexible state. Then, as shown in FIG. 8B, the thermoplastic can be re-shaped and re-cured to maintain a new shape as desired, which can also be done multiple times.

Figure 9A:
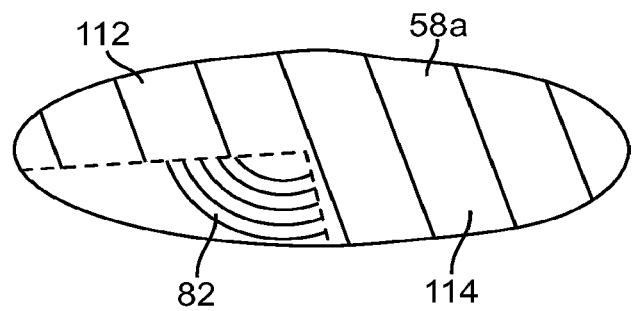
FIGS. 9A-9F are perspective views with cut-outs of another alternative embodiment of a charging head, featuring a plurality of hinged sections, used in the SCS system of FIG. 1.
Figure 9B:
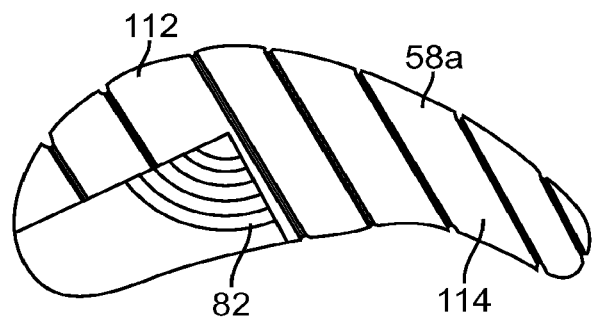
Figure 9C:
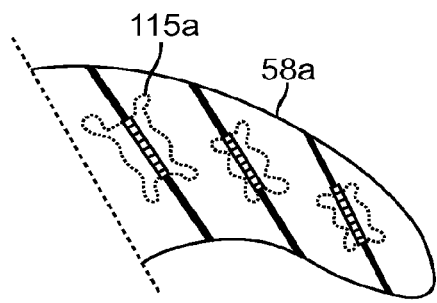
Figure 9D:
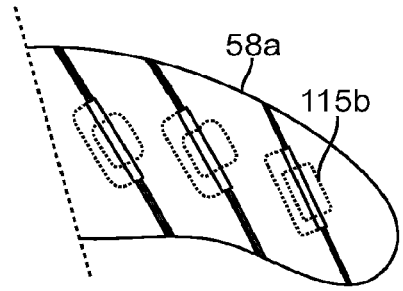
Figure 9E:
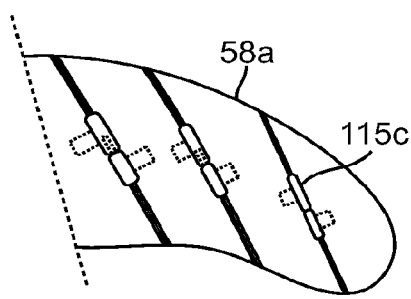
Figure 9F:
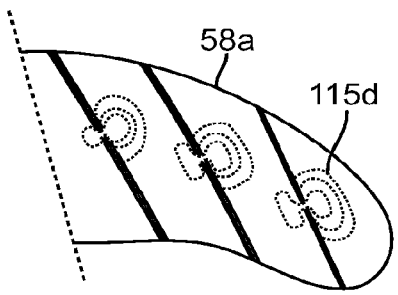

Referring to FIGS. 9A-9F, another embodiment of a charging head 58 includes a bendable shell 112 that can be selectively shaped. The shell 122 has a plurality of hinged sections 114 that pivot against each other as the shell 112 is bent in shaping the charging head 58. For example, the shell 112 may be bent from a flat configuration to a crescent configuration (FIG. 9B). The hinged sections 114 may employ any of a variety of suitable hinge mechanisms known in the art that allow the hinged sections 114 to pivot against each other while providing a wide range of movement, such as a butterfly hinge 115a (FIG. 9C), a flush hinge 115b (FIG. 9D), or a barrel hinge 115c (FIG. 9E), or also a joint assembly such as a ball and socket joint 115d (FIG. 9F). The hinge designs may also include gear teeth or other components known in the art to control the hinging movement of the hinged sections 114 and to help maintain the shell 112 in a desired shape. The shell 112 may be composed of any of a variety of suitable materials that are sufficiently rigid to help stabilize the shell 112 without interfering with the charging action of the external charger 18, such as plastic, ceramic, or a combination of these and/or similar materials.

Figure 10:
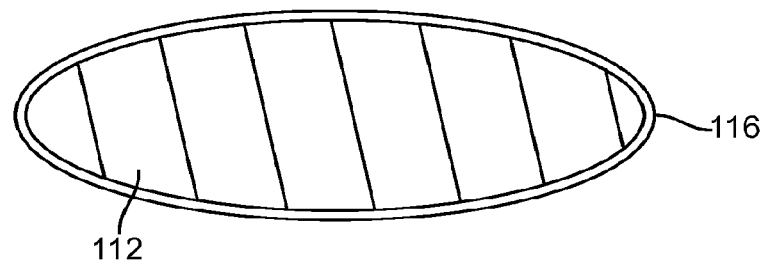
FIG. 10 is a perspective view of an alternative embodiment of the charging head shown in FIGS. 9A-9F.

As an additional feature, the shell 112 may further include a skin 116 that substantially covers the outer surface of the shell 112, as shown in FIG. 10, or alternatively, the inner surface of the shell 112 or both the inner and outer surfaces of the shell 112. The skin 116 helps to protect the coil 82 and other electrical components in the charging head 58, such that if the shell 112 is bent enough to form an open space between the hinged sections 114, or if the shell 112 cracks or breaks, the electrical components remain covered. The skin 116 is preferably composed of one or more waterproof materials that are sufficiently flexible to accommodate bending of the shell 112, such as plastic, rubber, polyurethane, or a combination of these and/or similar materials.

Figure 11:
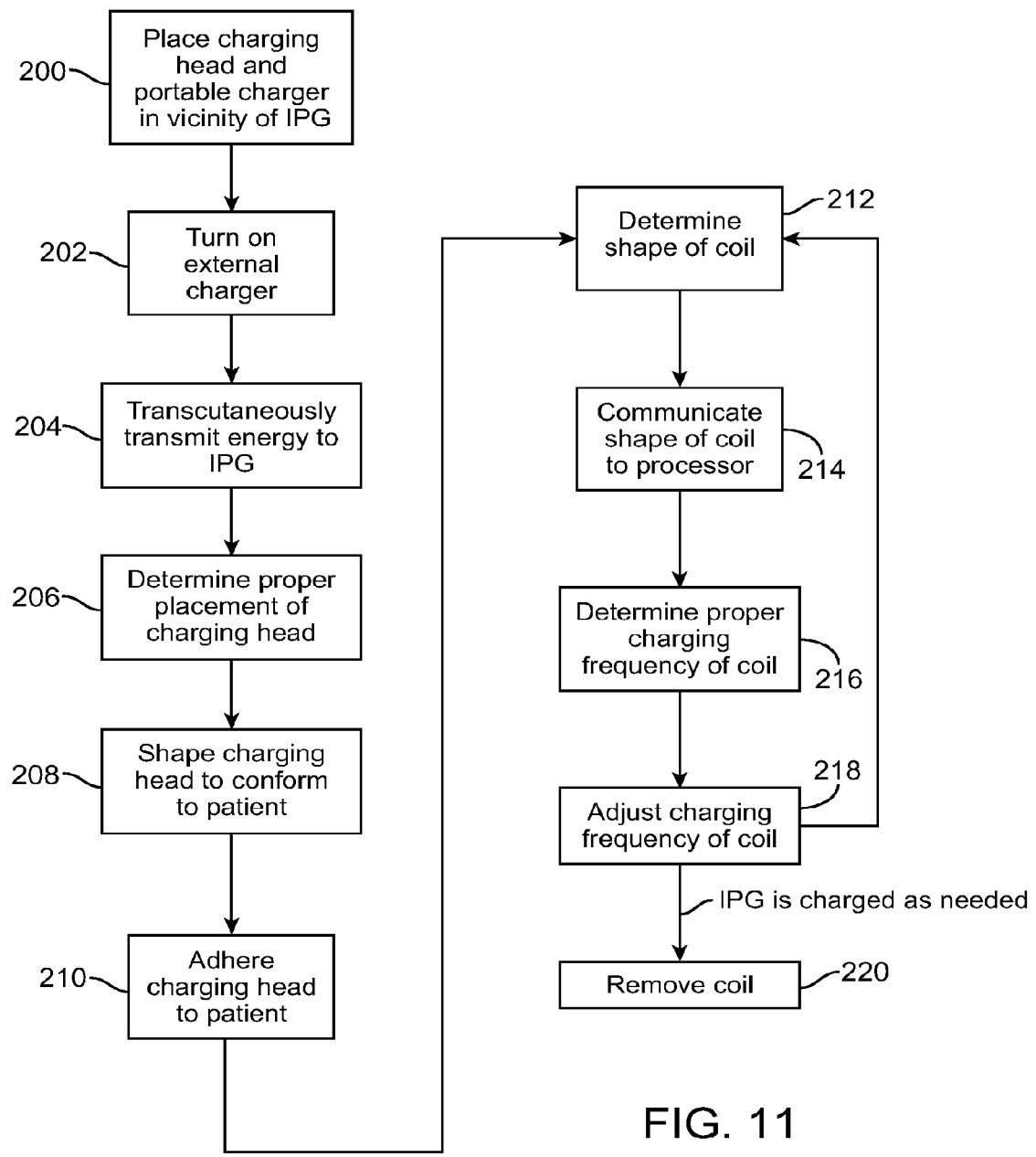
FIG. 11 is a flow diagram of a method used by the external charger to charge the implantable pulse generator.
Figure 12:
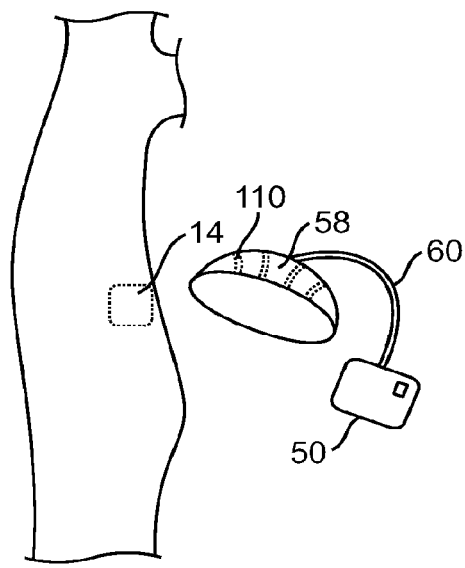
FIGS. 12 and 13 are perspective views of a method of using the external charger in the SCS system of FIG. 1, and in particular using the charging head illustrated in FIGS. 5A and 5B.
Figure 13:
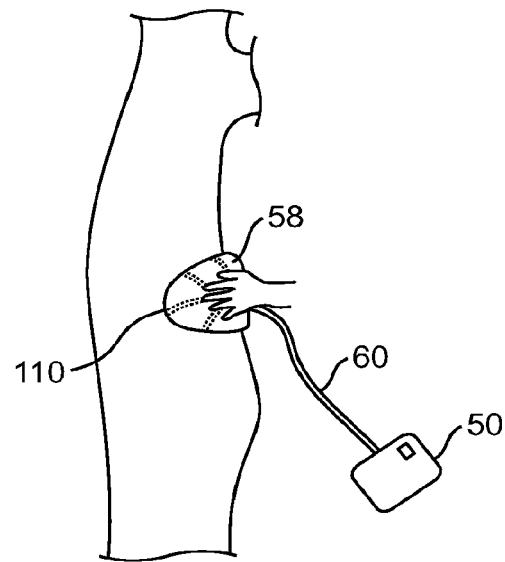

Having described the structure and function of the charging system, one method of using the external charger 18 to recharge the IPG 14 will now be described with reference to FIGS. 11-13. First, the charging head 58 and the portable charger 50 are placed in the general vicinity of the implanted IPG 14 (step 200), as shown in FIG. 12. Next, the portable charger 50 is turned on (step 202), thereby transcutaneously transmitting charging energy from the charging head 58 to the IPG 14 to charge the IPG 14, as described above (step 204). The proper placement of the charging head 58 is then determined (step 206) to help optimize charging efficiency of the IPG 14. For example, in the embodiment including an alignment (or misalignment) indicator, audible or tactile indications from the indicator are used to determine proper alignment between the charging head 58 and the IPG 14. The charging head 58 is then shaped to conform to the surface of the patient where the charging head 58 will be attached (step 208), as shown in FIG. 13.

Figure 14:
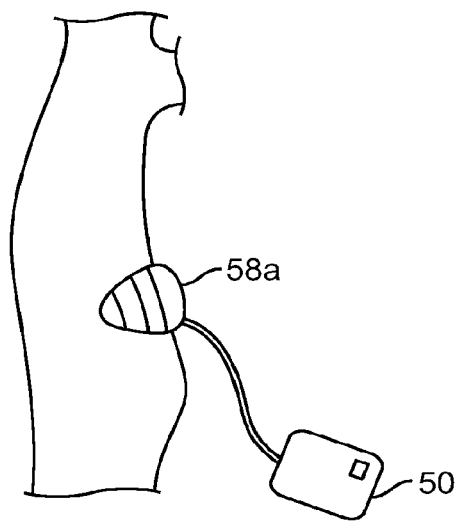
FIG. 14 is a perspective view of a method of using the external charger in the SCS system of FIG. 1, and in particular using the charging head illustrated in FIGS. 8A-8F.

In this case where the charging head 58 illustrated in FIGS. 5A and 5B is used, the support members 110 help maintain the shape of the charging head 58 on the patient. For the embodiment in which the material of the charging head 58 is cured, the charging head 58 may be first shaped on the patient, after which the material is cured, and then the charging head 58 is returned for use on the patient. To charge the IPG 14 using the embodiment of the charging head 58 illustrated in FIGS. 9A and 9B, the charging head 58 is bent to conform to the patient, causing the hinged sections 114 to pivot as the charging head 58 is bent, as shown in FIG. 14.

The charging head 58 is then adhered to the patient (step 210). The charging head may be adhered to the patient using any suitable form of adhesive, wherein the form of adhesive is preferably comfortable for the patient. For example, the charging head may include double-sided medical tape that can be added and removed as needed, or a moisture-activated adhesive patch (not shown), wherein a small amount of liquid is applied to the patch for adherence to the patient. The patch may be selectively placed on different areas or fixed on one area of the charging head 58. Also, opposing ends of the charging head may be joined by a suitable adhesive, for example, to secure the charging head around a patient's limb, neck, or head. The charging head may also be connected to a strap (not shown) that is secured to the patient by a snap, button, or hook-and-loop attachment, as examples, for additional support on the patient.

The charging frequency of the energy may then be adjusted based on the shape of the coil 82 in the charging head 58. In particular, the sensors 118 determine the shape of the coil 82 (step 212) and communicate any change in shape to the processor 120 (step 214). The processor 120 determines the proper charging frequency of the coil 82 to maintain charging efficiency (step 216) and causes the coil 82 to adjust to such frequency (step 218). The charging frequency may be adjusted based on values stored in memory 102 in the processor 120. If further shaping or movement of the charging head 58 occurs to change the coil 82 shape, the sensors 118 will determine the new shape of the coil 82 and communicate the new shape to the processor 120, which in turn will adjust the charging frequency of the coil 82. The charging head 58 thus continues to charge the IPG 14 as needed, preferably until the IPG 14 is fully charged, after which the charging head 58 is removed from the patient (step 220).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of charging an implanted medical device, comprising:
    placing an external charging head on a surface of a patient in the general vicinity of the implanted medical device;
    shaping the external charging head to conform to the surface of the patient;
    sensing the shape of the external charging head as it conforms to the surface of the patient;
    determining a charging frequency based on the sensed shape of the external charging head; and
    transcutaneously transmitting energy from external charging head to the implanted medical device in accordance with the determined charging frequency, thereby charging the implanted medical device.

2. The method of claim 1, further comprising adhering the external charging head to the surface of the patient.

3. The method of claim 2, wherein the external charging head is adhered to the surface of the patient with a moisture-activated adhesive patch.

4. The method of claim 1, further comprising generating a user-discernible signal when the external charging head and the implanted medical device are aligned with each other.

5. The method of claim 1, further comprising:
    changing the shape of the external charging head to conform to the surface of the patient;
    sensing the changed shape of the external charging head as it conforms to the surface of the patient;

determining another charging frequency of the external charging head based on the sensed changed shape of the external charging head; and transcutaneously transmitting energy from external charging head to the implantable medical device in accordance with the determined other charging frequency.

6. The method of claim 1, wherein sensing the shape of the external charging head comprises sensing a resistance, and the charging frequency is determined by recalling from a memory device the shape of the external charging head correlated to the sensed resistance, and determining the charging frequency based on the correlated shape of the external charging head.

7. The method of claim 1, further comprising:

generating a signal in response to the sensing of the shape of the external charging head; and conveying the signal to a processor that determines the charging frequency based on the conveyed signal.

\* \* \* \* \*